United States Patent [19]

Snoke et al.

[11] Patent Number: 5,846,221
[45] Date of Patent: Dec. 8, 1998

[54] STEERABLE CATHETER HAVING DISPOSABLE MODULE AND STERILIZABLE HANDLE AND METHOD OF CONNECTING SAME

[75] Inventors: Phillip Jack Snoke, Atlanta; Michael J. Mark, Suwanee; David Scott Rowley, Smyrna, all of Ga.

[73] Assignee: Catheter Imaging Systems, Inc., Atlanta, Ga.

[21] Appl. No.: 78,295

[22] Filed: May 13, 1998

Related U.S. Application Data

[62] Division of Ser. No. 598,804, Feb. 9, 1996, Pat. No. 5,820,590.

[51] Int. Cl.$^6$ .................................................. A61M 37/00
[52] U.S. Cl. .............................. 604/49; 604/95; 604/283
[58] Field of Search ................................ 604/95, 49.53, 604/27, 28, 280, 281, 283; 128/642, 656–658; 600/146–152, 139

[56] References Cited

U.S. PATENT DOCUMENTS

| | | | |
|---|---|---|---|
| Re. 33,854 | 3/1992 | Adair | 128/6 |
| D. 243,115 | 1/1977 | Ziegler et al. | D24/138 |
| D. 280,280 | 8/1985 | Haltmon et al. | D24/107 |
| D. 338,958 | 8/1993 | Jensen | D24/133 |
| D. 343,678 | 1/1994 | Snoke et al. | 604/95 |
| D. 349,340 | 8/1994 | Snoke et al. | D24/138 |
| 922,985 | 10/1909 | Wappler . | |
| 3,470,876 | 10/1969 | Barchiton | 128/348 |
| 3,500,820 | 3/1970 | Almen | 604/95 |
| 3,605,725 | 9/1971 | Bentov . | |
| 3,625,200 | 12/1971 | Muller | 128/2.05 |
| 3,773,034 | 11/1973 | Burns et al. | 604/95 |
| 3,788,304 | 1/1974 | Takahashi | 128/6 |

(List continued on next page.)

FOREIGN PATENT DOCUMENTS

| | | |
|---|---|---|
| 0 343 094 | 1/1989 | European Pat. Off. . |
| 0 370 158 | 5/1990 | European Pat. Off. . |
| 0389453 | 9/1990 | European Pat. Off. . |
| 0 489 937 | 6/1992 | European Pat. Off. . |
| 489937 | 6/1992 | European Pat. Off. . |
| 990417 | 9/1951 | France . |
| 2 655 548 | 6/1991 | France . |
| 1213571 | 3/1966 | Germany . |
| 3916288 | 11/1989 | Germany . |
| 4304530 | 8/1993 | Germany . |
| WO88/00810 | 2/1988 | WIPO . |
| WO 9 101 772 | 2/1991 | WIPO . |
| WO91/11213 | 8/1991 | WIPO . |

*Primary Examiner*—John D. Yasko
*Attorney, Agent, or Firm*—Allen, Dyer, Doppelt, Milbrath & Gilchrist, P.A.

[57] ABSTRACT

A catheter and methods are provided for inserting at least portions thereof into a vessel, cavity, or tissue of a human body to thereby provide manipulation of a distal portion of the catheter when positioned within a vessel, cavity, or tissue. The catheter preferably has a module which includes an elongate tube having at least one lumen extending from a distal end to a proximal end of the tube, a module interface connected to the proximal end of the tube, and a deflector connected to the tube for deflecting the distal portion of the elongate tube. A handle detachably connects to the module and is configured to be readily held in the hand of a user. The handle has a body which includes a wall positioned in and extending transversely across distal portions of the body. The wall has an outer surface thereof defining an exterior portion of the body and a first cavity formed within the body. Preferably, the body detachably and coextensively connects to the module interface through the outer surface of the wall. A controller is connected to the body and detachably connects to the deflector of the module for responsively controlling the deflector to thereby manipulate distal portions of the elongate tube. The controller and the deflector connect to define a unitary catheter manipulator extending from the first cavity, through the wall, and to the tube for manipulating a distal portion of the catheter when positioned within a vessel, cavity, or tissue.

8 Claims, 5 Drawing Sheets

U.S. PATENT DOCUMENTS

| | | | |
|---|---|---|---|
| 3,831,017 | 8/1974 | Auer | 240/2 |
| 3,892,228 | 7/1975 | Mitsui | 128/4 |
| 3,948,251 | 4/1976 | Hosono | 128/4 |
| 4,273,111 | 6/1981 | Tsukaya | 128/6 |
| 4,279,245 | 7/1981 | Takagi et al. | 128/4 |
| 4,327,723 | 5/1982 | Frankhouser | 128/214.4 |
| 4,344,092 | 8/1982 | Miller | 358/217 |
| 4,353,358 | 10/1982 | Emerson | 128/4 |
| 4,390,012 | 6/1983 | Mizumoto | 128/4 |
| 4,413,278 | 11/1983 | Feinbloom | 358/93 |
| 4,417,886 | 11/1983 | Frankhouser et al. | 604/53 |
| 4,421,106 | 12/1983 | Uehara | 128/4 |
| 4,433,675 | 2/1984 | Konoshima | 128/6 |
| 4,475,539 | 10/1984 | Konomura | 128/6 |
| 4,483,326 | 11/1984 | Yamaka et al. | 128/4 |
| 4,515,592 | 5/1985 | Frankhouser | 604/163 |
| 4,539,586 | 9/1985 | Danna et al. | 358/98 |
| 4,543,090 | 9/1985 | McCoy | 604/95 |
| 4,545,374 | 10/1985 | Jacobson | 128/303 |
| 4,573,448 | 3/1986 | Kambin | 128/1 R |
| 4,577,621 | 3/1986 | Patel | 128/4 |
| 4,580,551 | 4/1986 | Siegmund et al. | 128/4 |
| 4,587,972 | 5/1986 | Morantte, Jr. | 128/660 |
| 4,589,404 | 5/1986 | Barathj et al. | 128/6 |
| 4,590,923 | 5/1986 | Watanabe | 128/6 |
| 4,601,284 | 7/1986 | Arakawa et al. | 128/6 |
| 4,607,021 | 8/1986 | Wheeler | 128/6 |
| 4,611,888 | 9/1986 | Prenovitz et al. | 350/96.22 |
| 4,625,713 | 12/1986 | Hiraoka | 128/4 |
| 4,644,960 | 2/1987 | Johans | 128/786 |
| 4,649,904 | 3/1987 | Kravter et al. | 128/6 |
| 4,651,202 | 3/1987 | Arakawa | 358/98 |
| 4,653,476 | 3/1987 | Bonnet | 128/4 |
| 4,713,057 | 12/1987 | Huttner et al. | 604/164 |
| 4,737,142 | 4/1988 | Heckele | 604/95 |
| 4,745,908 | 5/1988 | Warale | 128/6 |
| 4,748,969 | 6/1988 | Wardle | 128/4 |
| 4,750,475 | 6/1988 | Yoshihashi | 128/6 |
| 4,753,222 | 6/1988 | Morishita | 128/4 |
| 4,758,222 | 7/1988 | McCoy | 604/95 |
| 4,776,844 | 10/1988 | Ueda | 604/95 |
| 4,782,819 | 11/1988 | Adair | 604/280 |
| 4,791,912 | 12/1988 | Tashiro | 128/4 |
| 4,793,326 | 12/1988 | Shishido | 128/4 |
| 4,797,737 | 1/1989 | Yazawa | 358/98 |
| 4,799,496 | 1/1989 | Hargreaves et al. | 128/772 |
| 4,808,157 | 2/1989 | Coombs | 604/44 |
| 4,815,450 | 3/1989 | Patel | 128/6 |
| 4,834,710 | 5/1989 | Fleck | 604/171 |
| 4,844,053 | 7/1989 | Dittrich | 128/4 |
| 4,853,773 | 8/1989 | Hibino et al. | 358/98 |
| 4,867,529 | 9/1989 | Utsumi et al. | 350/96.25 |
| 4,884,133 | 11/1989 | Kanno et al. | 358/98 |
| 4,890,602 | 1/1990 | Hake | 128/4 |
| 4,893,613 | 1/1990 | Hake | 128/4 |
| 4,901,142 | 2/1990 | Ikuno et al. | 358/98 |
| 4,904,237 | 2/1990 | Janese | 604/28 |
| 4,905,666 | 3/1990 | Fukuda | 128/4 |
| 4,906,230 | 3/1990 | Maloney et al. | 604/95 |
| 4,911,148 | 3/1990 | Sosnowski et al. | 128/6 |
| 4,919,653 | 4/1990 | Martinez et al. | 604/117 |
| 4,920,413 | 4/1990 | Nakamura et al. | 358/98 |
| 4,924,856 | 5/1990 | Noguchi | 128/6 |
| 4,930,521 | 6/1990 | Metzger et al. | 128/786 |
| 4,933,816 | 6/1990 | Hug et al. | 362/32 |
| 4,934,340 | 6/1990 | Ebling et al. | 128/6 |
| 4,954,129 | 9/1990 | Giuliani et al. | 604/53 |
| 4,968,295 | 11/1990 | Neumann | 604/6 |
| 4,968,298 | 11/1990 | Michelson | 604/36 |
| 4,972,828 | 11/1990 | Ito | 128/4 |
| 4,973,312 | 11/1990 | Andrew | 604/158 |
| 4,973,329 | 11/1990 | Park et al. | 606/1 |
| 4,979,496 | 12/1990 | Komi | 128/4 |
| 4,983,165 | 1/1991 | Loiterman | 604/95 |
| 4,986,258 | 1/1991 | Cho et al. | 128/7 |
| 4,989,582 | 2/1991 | Sakiyama et al. | 128/6 |
| 4,996,974 | 3/1991 | Ciarlei | 128/4 |
| 5,004,456 | 4/1991 | Botterbusch et al. | 604/53 |
| 5,010,875 | 4/1991 | Kato | 128/6 |
| 5,024,655 | 6/1991 | Freeman et al. | 604/53 |
| 5,042,915 | 8/1991 | Akutsu et al. | 359/230 |
| 5,053,046 | 10/1991 | Janese | 606/215 |
| 5,058,568 | 10/1991 | Irion et al. | 128/4 |
| 5,084,043 | 1/1992 | Hertzman et al. | 606/3 |
| 5,085,631 | 2/1992 | Leighton | 604/28 |
| 5,090,959 | 2/1992 | Samson et al. | 604/96 |
| 5,101,807 | 4/1992 | Kawashima | 128/6 |
| 5,125,906 | 6/1992 | Fleck | 604/171 |
| 5,131,382 | 7/1992 | Meyer | 128/6 |
| 5,134,469 | 7/1992 | Uchimura | 358/98 |
| 5,143,475 | 9/1992 | Chikama | 403/291 |
| 5,167,221 | 12/1992 | Chikama | 128/4 |
| 5,188,594 | 2/1993 | Zilberstein | 604/51 |
| 5,195,541 | 3/1993 | Obenchain | 128/898 |
| 5,197,649 | 3/1993 | Bessler et al. | 227/179 |
| 5,199,417 | 4/1993 | Muller et al. | 128/6 |
| 5,199,950 | 4/1993 | Schmitt et al. | 604/95 |
| 5,215,105 | 6/1993 | Kizelshteyn et al. | 128/898 |
| 5,232,442 | 8/1993 | Johnson et al. | 604/51 |
| 5,267,573 | 12/1993 | Evans et al. | 604/95 |
| 5,273,535 | 12/1993 | Edwards et al. | 604/95 |
| 5,275,151 | 1/1994 | Shockey et al. | 128/4 |
| 5,342,299 | 8/1994 | Snoke et al. | 604/95 |
| 5,344,397 | 9/1994 | Heaven et al. | 604/95 |
| 5,354,266 | 10/1994 | Snoke | 604/28 |
| 5,396,880 | 3/1995 | Kagan et al. | 128/6 |
| 5,399,164 | 3/1995 | Snoke et al. | 604/95 |
| 5,415,158 | 5/1995 | Barthel et al. | 604/95 |
| 5,423,311 | 6/1995 | Snoke et al. | 128/6 |
| 5,437,636 | 8/1995 | Snoke et al. | 604/95 |
| 5,531,687 | 7/1996 | Snoke et al. | 604/95 |
| B1 453,958 | 12/1991 | Danna et al. | 358/98 |

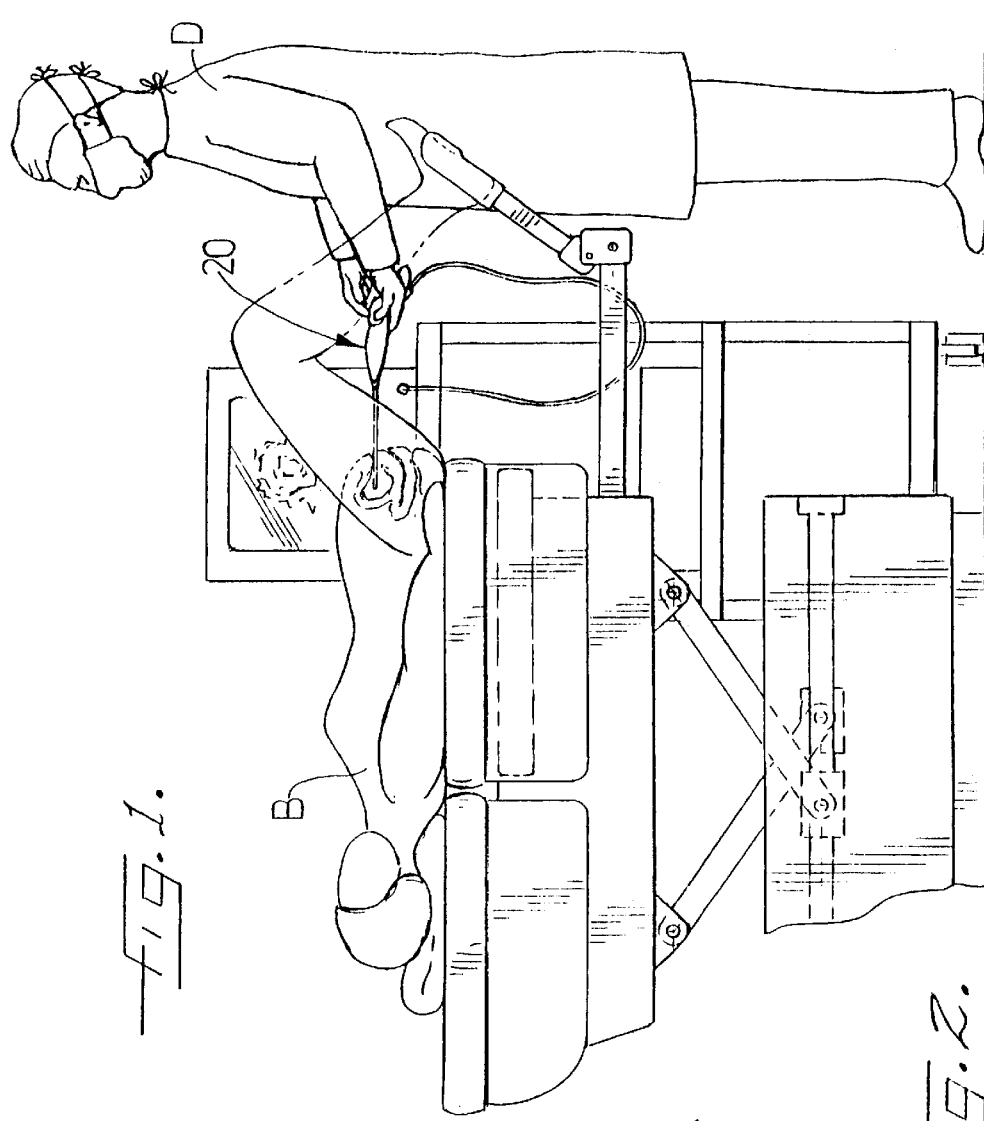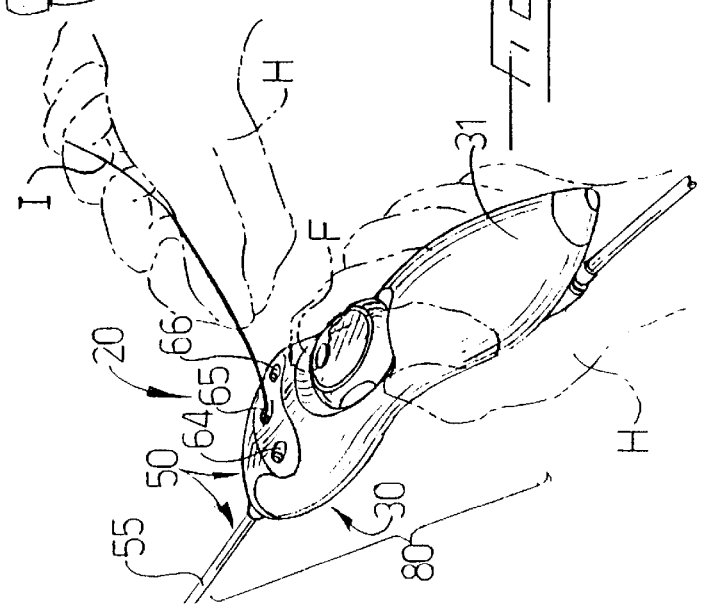

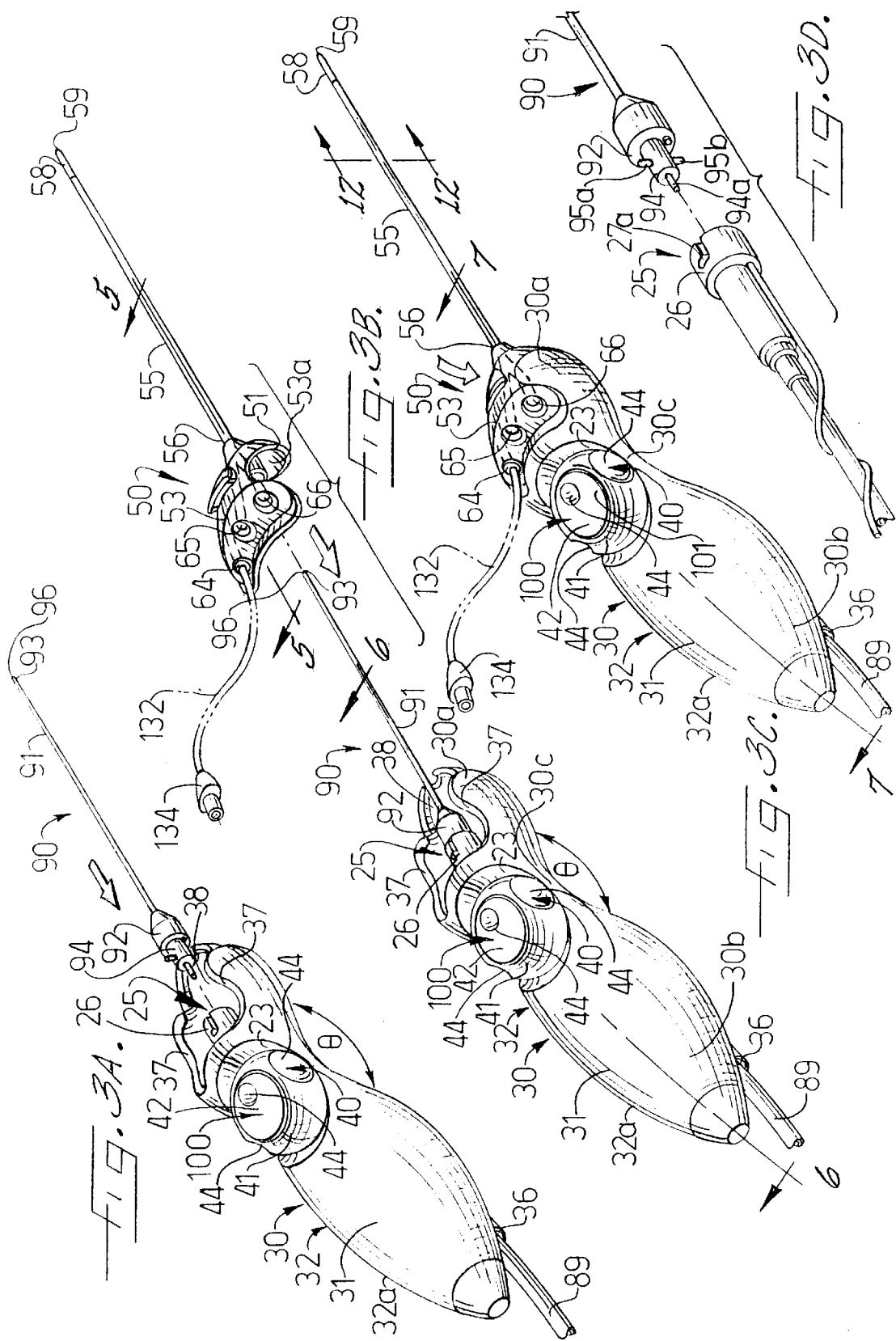

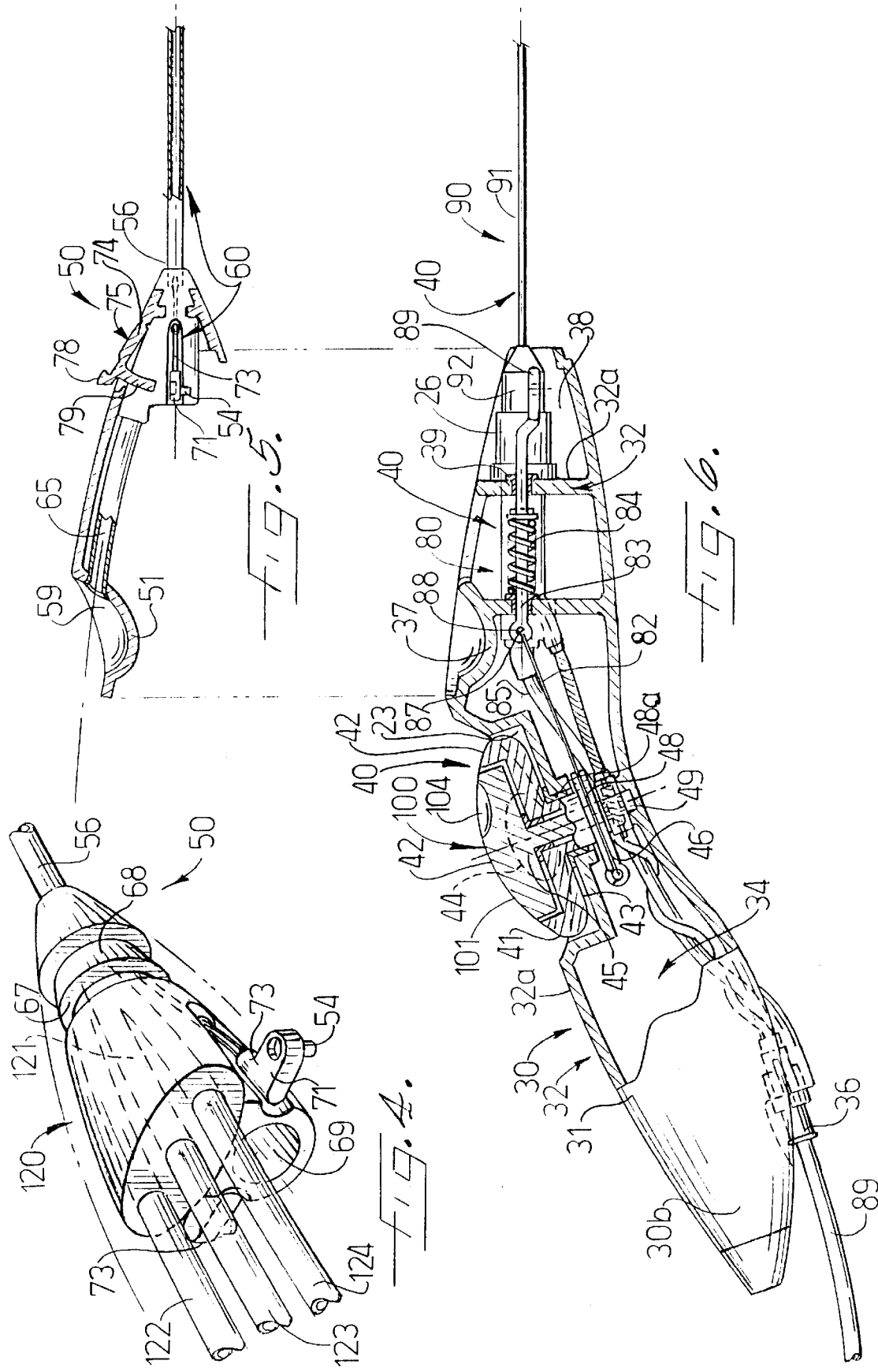

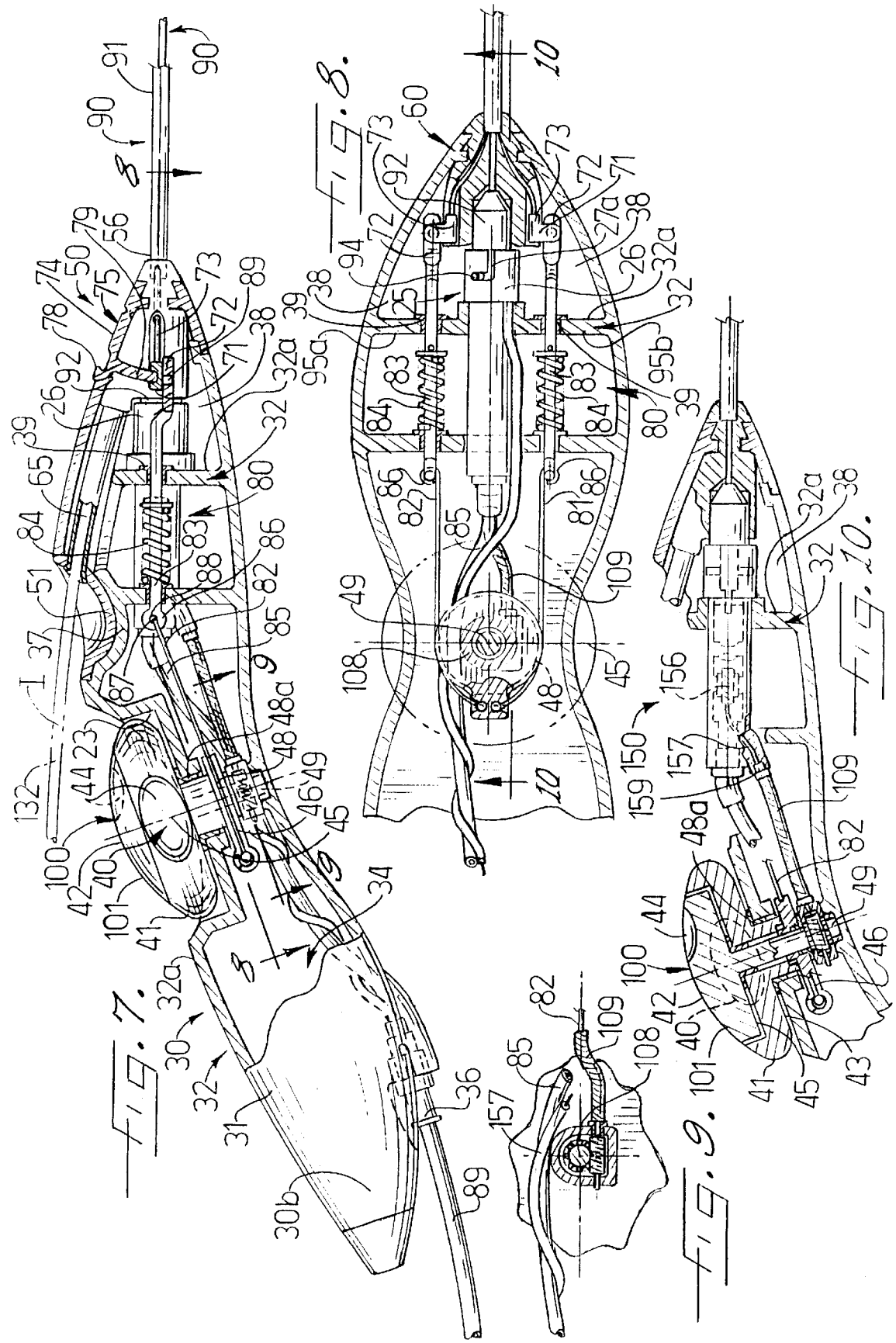

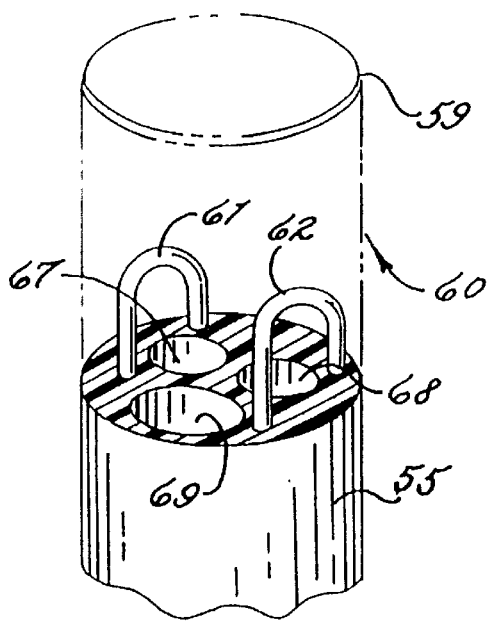
_Fig. 11._
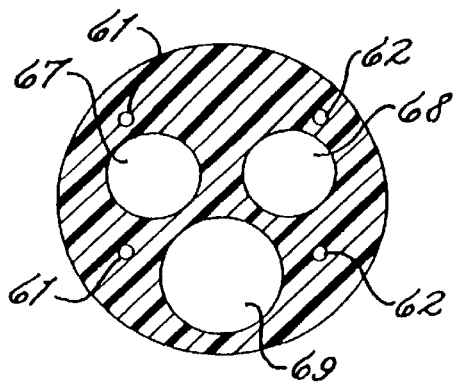
_Fig. 12._
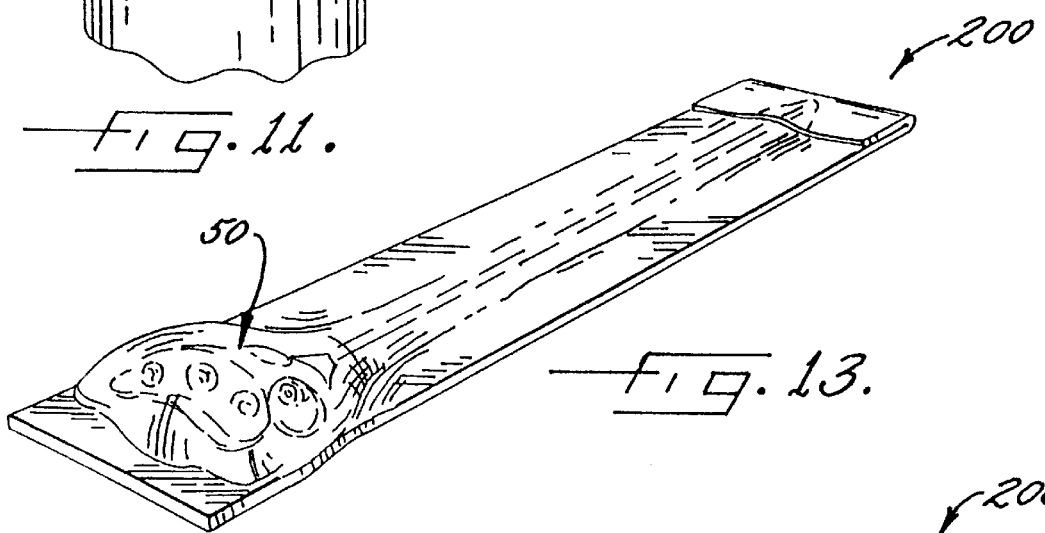
_Fig. 13._
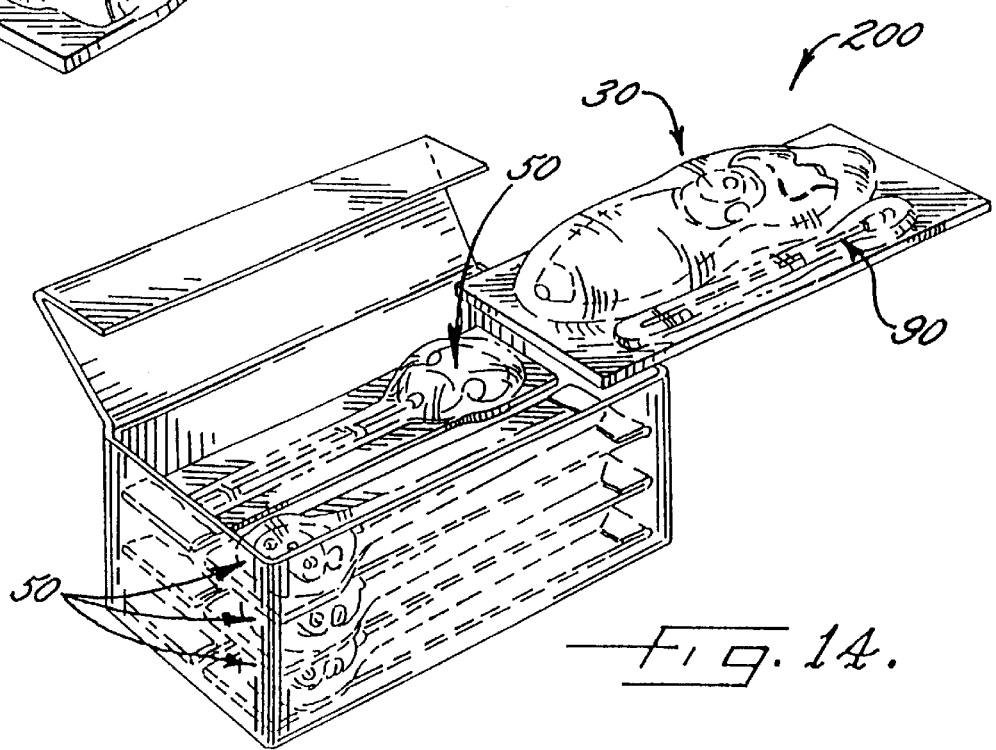
_Fig. 14._

STEERABLE CATHETER HAVING DISPOSABLE MODULE AND STERILIZABLE HANDLE AND METHOD OF CONNECTING SAME

This application is a division of Ser. No. 08/598,804 filed on Feb. 9, 1996 now U.S. Pat. No. 5,820,590.

RELATED APPLICATIONS

This application is related to and a continuation-in-part of four pending design applications: Ser. No. 29/046,932, filed Nov. 21, 1995 for Steerable Catheter; Ser. No. 29/048,898 filed Jan. 12, 1996 for Handle For Steerable Catheter; Ser. No. unassigned as of this filing date, Filed Jan. 12, 1996 for Steerable Catheter; and Ser. No. 29/048,899, filed Jan. 12, 1996 for Handle Interface For Steerable Catheter.

FIELD OF INVENTION

This invention relates generally to medical catheters and more specifically to steerable catheters for inserting into vessels, cavities, or tissue of the human body.

BACKGROUND OF THE INVENTION

Various commercially available endoscopes and steerable catheters exist for introducing a variety of surgical tools, fluids, and other materials such as radiographic contrast materials, angioplasty balloons, fiber optic scopes, laser lights, and cutting instruments into the vessels, cavities, or tissue of a human body. Also, various techniques and systems have been developed for guiding or steering the catheters or endoscopes in body vessels or cavities for use with these tools, fluids, and other materials. Therapeutic or diagnostic treatments may be made by inserting surgical instruments or fluid through a working channel or lumen of a catheter.

Catheters conventionally include a conduit or flexible tube for inserting into a cavity, duct, or vessel of the human body to allow fluids to pass therethrough or to allow instruments to be inserted through the tube. Catheters also have been developed with steering mechanisms to guide or manipulate the catheter such as seen in U.S. Pat. No. 5,199,950 by Schmitt et al. titled "Medical Instrument." Endoscopes are generally tools used to view within a portion of the anatomy through an open end of a tube. Flexible endoscopes have been constructed for use within "tube-like" portions or cavities of the anatomy (e.g., arteries, ureters, common bile duct). Endoscopes have been designed for the user to look directly through an objective lens or in conjunction with video cameras attached remotely to the scope for viewing a portion of the human body. Rod lens systems also have been used with some endoscopes to view images. In other endoscopes, the image is gathered at the distal end by a lens and transferred to a proximal objective lens using fiber optic bundles.

During use in medical procedures, endoscopes and steerable catheters are exposed to various viruses, bacteria, and harmful disease carrying media. These viruses and bacteria can be trapped in the endoscope or steerable catheter, particularly in lumens and transferred to subsequent patients or users. During use of these medical devices, microbes have also been trapped inside patient materials that remain in the endoscopes and become coated with lubricants and various organic materials in the endoscope. If not effectively eliminated, these materials can and have been transferred to other patients or medical personnel through subsequent use of the endoscope or steerable catheter. In the human body, enzymes and digestive processes work to release these internally trapped microbes from the lubricant coatings. These harmful microbes can infect the subsequent patients or medical personnel with dangerous or deadly diseases.

Sterilization methods have been employed on reusable medical devices, including various endoscopes and steerable catheters, in an attempt to disinfect and eliminate viruses and bacteria for subsequent use of the devices. For example, glutaraldehyde has been used to treat reusable endoscopes. Also, heat sterilization and other chemical disinfection have been employed to attempt to sterilize internally contaminated medical devices. Some endoscopes and steerable catheters contain very small and narrow working channels or lumens for performing intricate medical procedures. These small or narrow working channels or lumens are difficult to clean and sterilize. Further, research has shown that, in spite of attempts to sterilize endoscopes, endoscope lubricants can shield viruses, including HIV, from high-level disinfection. Disease transmissions have been documented for endoscopes used in diagnostic and surgical procedures even after treatment with chemicals such as glutaraldehyde. The instances of epidemics of various diseases, including new and old diseases, are rising due to the increasing density of human population and frequency of human contact. At the same time, the effectiveness of certain antibiotics is diminishing and the numbers of individuals with increased susceptibility to disease is on the increase. Technological advances have also increased the frequency of use of medical instruments which are difficult to clean, yet are not disposable. These factors have produced an environment where the likelihood of infection caused by passing disease causing viruses, bacteria, or other matter is rapidly increasing.

In addition to the problem of infection and transmission of disease, prior endoscopes and catheters by virtue of their design and materials have been intended for prolonged, repeated use. The precision of manipulation and movement in endoscopes and steerable catheters is essential for conducting the complicated medical procedures and diagnostics generally employed by such devices. Some repeated use endoscopes and steerable catheters have contained steering mechanisms to manipulate the endoscopes within the human body. These mechanisms have been complicated and required precision calibration. Further, these devices have also had to withstand sterilization with heat or chemicals. To accomplish these objectives, reusable endoscopes and steerable catheters have been made of steel or other durable metals which are costly.

To maintain integrity and precision, endoscopes and steerable catheters have generally been designed as intended for repeated, prolonged use. In spite of being designed for repeated use, however, these scopes such as laparoscopes, require replacement much more frequently than other visualization equipment such as cameras or light sources. A typical replacement cycle is one to two years. In high volume surgery centers, some scopes require replacement after a few weeks or months due to damage from mishandling or dropping. Repairing these endoscopes is also costly. The requirement of sterilization also adds additional cost to each medical procedure requiring additional chemicals and equipment.

Limited attempts have been made to provide a detachable reusable endoscope. One repeated use detachable-end endoscope with a detachable flexible shaft is described in U.S. Pat. No. 4,911,148 by Sosnowski et al. titled "Deflectable-End Endoscope With Detachable Flexible Shaft." This patent describes a flexible shaft assembly which connects to a handle subassembly to form an endoscope. The handle subassembly includes a hollow female bayonet connector which couples with a male connector in the shaft subassembly. The endoscope described in U.S. Pat. No. 4,911,148 by Sosnowski has a central opening extending from a proximal end to the distal end of the endoscope. A lens is positioned within the opening to provide appropriate magnification for an operator to manually view the distal end of the endoscope. This endoscope is also intended for reuse as both the shaft subassembly and handle subassembly are provided with watertight seals to prevent a compromise of internal components resulting from usage and sterilizations. The shaft subassembly, however, as described above, has some of the sterilization failures of previous technology and provides an awkward and inefficient manner for viewing the distal end of the endoscope.

In addition to the issues of disease transmission and disposability, numerous endoscopes have been designed which are bulky or difficult to use, requiring numerous hands or personnel. Hand-held catheters have been developed to provide the control and manipulation of the catheter for simultaneous use with surgical tools, fiber optic scopes, and fluids needed for medical operations, such as in U.S. Pat. No. 5,342,299 by Snoke et al. titled "Steerable Catheter." Many medical procedures, however, require passage of relatively straight instruments into the human body at an angle difficult to actuate relative to the position of the portion of the medical device in the medical practitioner's hand.

As stated, none of the prior catheter or endoscope systems utilized fiber optic imaging systems to view within a human body. These systems required the use of an endoscope or catheter in conjunction with an external camera for transmitting images from within a human body to an external monitor. These external cameras occupied limited space in the operating or examination rooms and were susceptible to breakage or contamination. Still further, these cameras needed to be designed to withstand required direct sterilization.

Charged-coupled devices ("CCD's") have been proposed for use with endoscopes allowing direct image capture at the distal tip of an endoscope. Such systems conventionally place a camera chip at the distal end of a scope such as a laparoscope are referred to as a "chip-on-a-stick." These chip-on-a-stick devices are used in conjunction with an external camera connected to the scope by a cable. These chip-on-a-stick devices have several problems associated with them. For example, the scope may become contaminated during a procedure and sterilization often cannot be adequately performed on the device because of the presence of the CCD chip. This CCD chip also makes the scope somewhat expensive, especially where contamination occurs and sterilization is not possible without damaging the chip.

In chip-on-a-stick systems, the chip-on-a-stick generally would not be susceptible to sterilization at the tip of the endoscope because the camera chip is positioned on or around the tip. These external cameras also require space in shipping and storage. Prior endoscopes or steerable catheters which utilized fiber optic technology also often had an external focus mechanism associated with the external camera. This would require the practitioner to look or reach away from the area of the procedure to focus the image being viewed within the human body.

SUMMARY OF THE INVENTION

The present invention solves the aforementioned problems by providing a steerable catheter and methods including a reusable handle having a body and control means detachably connected to the interface of a disposable module which has an elongate tube including at least one lumen and deflecting means to provide a steerable catheter having a disposable module and a sterilizable handle for inserting at least portions thereof into a vessel, cavity, or tissue of a human body to thereby provide manipulation of a distal portion of the catheter when positioned within a vessel, cavity, or tissue. The present invention advantageously provides a steerable catheter having a disposable module and a sterilizable handle to eliminate or reduce the problem of disease transmission by providing a detachable steerable catheter including a disposable module designed for a single use which contains the difficult to sterilize working channels or lumens which can be utilized in conjunction with a reusable handle which can be effectively sterilized after each use. A detachable steerable catheter preferably includes a module having an elongate tube which is disposable after each use.

The present invention also advantageously provides a detachable steerable catheter having a a module including an elongate tube having at least one lumen within the tube with the module being easily detachably connected to a reusable handle which can be repeatedly sterilized to provide a cost-effective medical device which greatly reduces the possibility of transmission of disease from repeated use of the device. The present invention further advantageously provides a cost-effective disposable steerable catheter which retains the integrity and accuracy required during surgical uses. By providing a steerable catheter having a disposable module and a sterilizable handle the cost-per-procedure is reduced, and a reusable, easily sterilized handle according to the present invention retains the necessary precision which instills confidence in the medical practitioner due to its construction and ergonomic characteristics.

In accordance with the present invention, a steerable catheter having a disposable module and a sterilizable handle is provide for use in human body vessels, cavities, or tissue. The detachable steerable catheter preferably includes a module including an elongate tube having at least one lumen extending from a distal end to a proximal end of said tube, a module interface connected to the proximal end of said tube, and deflecting means connected to said tube for deflecting the distal portion of said elongate tube. The detachable steerable catheter further has a handle detachably connected to the module and configured to be readily held in the hand of a user. The handle preferably includes a body having a wall positioned in distal portions of the body. The wall has an outer surface defining an exterior portion of the body. The handle also has a first cavity formed within the body. The body is detachably and coextensively connected to the module interface through the outer surface of the wall. The handle also includes control means connected to the body and detachably connected to said deflecting means of the module for responsively controlling the deflecting means to thereby manipulate distal portions of the elongate tube. The control means and the deflecting means are connected to define a unitary catheter manipulation means which extends from the first cavity, through the wall, and to the tube for manipulating a distal portion of the catheter when positioned within a vessel, cavity, or tissue.

This steerable catheter having a disposable module and a sterilizable handle is for inserting at least portions thereof into a vessel, cavity, or tissue of a human body to thereby provide manipulation of a distal portion of the catheter when positioned within a vessel, cavity, or tissue. In an illustrative embodiment, the outer surface of the wall and a lower surface of the module interface also detachably connect to define a second cavity. The control means and the deflecting means are detachably connected within the second cavity so that the unitary catheter manipulation means extends from the first cavity, through the wall, through the second cavity, and to the tube for manipulating a distal portion of the catheter when positioned within a vessel, cavity, or tissue.

The present invention also includes methods of connecting and using a catheter. A method of detachably connecting a catheter having a handle which includes a body and a detachable module which includes an elongate tube having at least one lumen extending therethrough is provided by the present invention. This method preferably includes connecting a fiberscope to a distal end portion of the body of the handle, positioning the fiberscope into the at least one lumen of the tube of the module, and connecting the module to the body of the handle for viewing portions of a vessel, cavity, or tissue when a distal end of the tube is positioned therein.

The catheter and methods of the present invention further provide a detachable catheter with a reusable fiber optic scope which can be detachably connected to the handle and sealed within the detachable module during a medical procedure. A steerable catheter having a disposable module and a sterilizable handle according to the present invention also can advantageously be provided in a kit which, for example, includes a plurality of detachable, disposable modules and a reusable handle and fiber optic scope to be used with the disposable modules. The handle of a steerable catheter having a disposable module and a sterilizable handle according to the present invention can further include an angled handle that provides entry to positions of the human body while allowing the medical practitioner to grasp the steerable catheter in an advantageous hand position. A detachable steerable catheter can also advantageously include a camera mounted internally in the handle of the catheter wherein the handle can be sterilized with the camera therein, and the camera is protected from breakage or contamination therein. A steerable catheter and methods according to the present invention further can provide a steerable catheter having a focus means positioned on the handle of the catheter for focusing the internal camera positioned within the handle. A steerable catheter and methods of the present invention also advantageously provide a disposable module and a sterilizable handle having a focus wheel and control wheel disposed such that the focus wheel and control wheel can be simultaneously adjusted by the same hand of the practitioner.

BRIEF DESCRIPTION OF THE DRAWINGS

Some of the objects and advantages of the present invention having been stated, others will become apparent as the description proceeds when taken in conjunction with the accompanying drawings as follows:

FIG. 1 illustrates an environmental view of a medical procedure being conducted on a patient using a steerable catheter having a disposable module and a sterilizable handle according to the present invention positioned within an opening in the urological region of a human body by a medical practitioner for a therapeutic treatment of a problem area;

FIG. 2 illustrates an environmental perspective view of a steerable catheter having a disposable module and a sterilizable handle being held by the hand of a medical practitioner while simultaneously controlling an imaging system and manipulating a distal end portion of the catheter according to an embodiment of the present invention;

FIG. 3A illustrates a perspective view of a steerable catheter having a disposable module and a sterilizable handle according to the present invention showing a fiber optic scope being detachably connected to the handle;

FIG. 3B illustrates a perspective view of a steerable catheter having a disposable module and a sterilizable handle according to the present invention showing the fiber optic scope detachably connected to the handle and the module being positioned to slide over the fiber optic scope to detachably connect to the handle;

FIG. 3C illustrates a steerable catheter having a disposable module and a sterilizable handle according to the present invention having a detachable connected fiber optic scope positioned within the module and having the module positioned to detachably connect to the handle;

FIG. 3D illustrates an exploded perspective view of an imaging interface including an imaging capture device and a fiber optic scope of a steerable catheter according to the present invention;

FIG. 4 illustrates an enlarged perspective sectional view of a steerable catheter having a disposable module and a sterilizable handle according to the present invention showing a module interface of the module having medical instruments inserted within a lumen of the module;

FIG. 5 illustrates a cross-sectional view taken along line 5—5 of FIG. 3B showing a module of a steerable catheter detached from a handle according to an embodiment of the present invention;

FIG. 6 illustrates a cross-sectional view taken along line 6—6 of FIG. 3B showing a handle with a detachably connected fiber optic scope of a detachable steerable catheter according to the present invention having an imaging cable detachably connected to the handle;

FIG. 7 illustrates a side view taken according to line 7—7 of FIG. 3C showing an embodiment of a steerable catheter according to the present invention having a module and a fiber scope detachably connected to a handle with the fiber scope positioned within the module and having a medical instrument inserted within an access port and working lumen of the catheter;

FIG. 8 illustrates a top view taken along line 8—8 of FIG. 7 of a steerable catheter having a disposable module and a sterilizable handle according to the present invention showing a controller means detachably connected to a deflector of the module;

FIG. 9 illustrates a top view taken along line 9—9 of FIG. 7 showing an imaging interface cable and a focus cable connected to a shaft of a focus wheel and a focus controller disposed within a handle of a detachable steerable catheter according to the present invention;

FIG. 10 illustrates a side view taken along line 10—10 of FIG. 8 showing a steerable catheter having a disposable module and a sterilizable handle according to the present invention including an imaging system disposed within the handle;

FIG. 11 illustrates an enlarged cross sectional view taken along line 11—11 of FIG. 3C illustrating working lumens, a fiber optic scope lumen, deflecting wires, and an outer circumference of an elongate tube of a catheter according to the present invention;

FIG. 12 illustrates an enlarged fragmentary view of a distal portion of a catheter according to the present invention illustrating the insertion of deflecting wires within the catheter and showing a top of an elongate tube in phantom view;

FIG. 13 illustrates a sealed disposable module of a detachable steerable catheter according to the present invention for use in a kit; and FIG. 14 illustrates a steerable catheter having a disposable module and a sterilizable handle forming a kit according to the present invention including an individually packaged handle, fiber scope, and a plurality of modules within a single secondary package for distribution.

DETAILED DESCRIPTION

The present invention now will be described more fully hereinafter with reference to the accompanying drawings in which preferred embodiments of the invention are shown. This invention may, however, be embodied in many different forms and should not be construed as limited to the illustrated embodiments set forth herein; rather, these illustrated embodiments are provided so that this disclosure will be thorough and complete and will fully convey the scope of the invention to those skilled in the art. Like numbers refer to like elements throughout.

With further reference to the drawings, FIG. 1 illustrates an environmental view of a disposable steerable catheter 20 according to the present invention being used by a medical practitioner or doctor D in a medical procedure on a human body B. This embodiment of a disposable steerable catheter 20 is for inserting at least portions thereof into a vessel, cavity, or tissue of the human body B to thereby provide manipulation of a distal portion of the catheter 20 therein and to perform medical procedures using this catheter 20. The detachable and disposable steerable catheter 20 enables the medical practitioner D to insert medical instruments and fluids into a human body B and to view images from therein. Medical, surgical, and diagnostic procedures can be performed using a steerable catheter 20 having a disposable module 50 and a sterilizable handle 30 according to the present invention. Particularly, FIG. 1 shows the insertion of a detachable steerable catheter 20 according to the present invention into the urological canal during surgery. Procedures in other regions of the body could also effectively utilize the steerable catheter 20 having a disposable module 50 and a sterilizable handle 30 according to the present invention including procedures in the epidural region, the sinus cavity and/or nose region, the brain region, and other regions of the human body B.

As illustrated in FIGS. 3A–3D, the detachable steerable catheter 20 according to the present invention has a handle 30 detachably connected to a module 50. At least a distal portion 30a of the handle 30, and preferably the distal portion 30a and a bulbous portion 30b, has a bulbous shape. The handle 30 also is preferably configured to be readily held in the hand H of a user as shown in FIG. 2. More specifically, the detachable steerable catheter 20 has a module 50 including an elongate tube 55 having at least one lumen 67, 68, 69 (FIG. 12) preferably extending from a distal end portion 58 to a proximal portion 56 of the tube 55 as best shown in FIGS. 3B and 12. The module 50 also includes a module interface 53 connected to the proximal portion 56 of the tube 55 and deflecting means, e.g., deflector 60, associated with and preferably connected to the tube 55 for deflecting the distal end portion 58 of the elongate tube 55 as shown in FIGS. 5, 11, and 12. The deflecting means 60 preferably includes a pair of steering wires 61, 62 positioned within and coaxially extending the substantial length of the tube 55. It will be understood by those skilled in the art, however, that other types of deflectors 60 may be used as well.

The handle 30 has a body 31 including a wall 32 positioned in distal portions of the body 31 as shown in FIG. 3A. The wall 32 has an outer surface 32a defining an exterior portion of the body 31 without the module 50 connected thereto. The body 31 further includes a first cavity 34 positioned within the body 31 as shown in FIG. 6. The body 31 preferably is detachably and coextensively connected to the module interface 53 through the outer surface 32a of the wall 32.

The handle 30 also has control means, e.g., controller 40, connected to the body 31 and detachably connected to deflecting means 60 of the module 50 as shown in FIGS. 7–10. The control means 40 is positioned to responsively control the deflecting means 60 to thereby manipulate distal end portions 58 of the elongate tube 55. The control means 40 and deflecting means 60 are connected to define a unitary catheter manipulation means, e.g., manipulator 80, extending from the first cavity 34 through the wall 32 into the tube 55 for manipulating a distal end portion 58 of the catheter 20 when positioned within a vessel, cavity, or tissue of the human body B.

FIG. 7 illustrates an embodiment of a steerable catheter 20 having a disposable module 50 and a sterilizable handle 30 according to the present invention wherein the outer surface 32a of the wall 32 of the body 31 and a lower inner surface 53a of the module interface 53 come together to form a second cavity 38. The control means 40 and deflecting means 60 are detachably connected within the second cavity 38 and to the tube 55 as shown in FIG. 7. The unitary catheter manipulation means 80 extends from the first cavity 34 through the wall 32 and through the second cavity 38 into the tube 55 for manipulating a distal end portion 58 of a catheter 20 when positioned within a vessel, cavity, or tissue.

As best illustrated in FIGS. 3A, 3B, and 3D, a fiber optic scope 90 is also connected to an imaging interface 25 of an imaging system 24 positioned in the body 31 of the handle 30. The imaging interface 25 is preferably positioned within the second cavity 38 as shown in FIG. 10. The fiber optic scope 90 preferably is a fiber optic scope 90 used to transmit light from an external light source to within the human body B to illuminate a vessel, cavity, or tissue as well as to receive images captured within the human body B. The fiber optic scope 90 provided according to the present invention preferably is reusable and able to be repeatedly sterilized. Upon connection of the module 50 and handle 30, the second cavity 38 preferably is sealed by the connection of the peripheral edge portions 51 of the module 50 and the edge portions 37 of the handle 30. The connection of the fiber optic scope 90 to the imaging interface is thus protected within this second cavity 38.

The handle 30 is also provided to be sterilized and used repeatedly. The body 31 of the handle 30 preferably is constructed of a suitable material which can withstand heat sterilization temperatures and chemical sterilization as understood by those skilled in the art. These sterilization methods are understood by those skilled in the art and, therefore, will not be discussed further. The handle 30 is also constructed of a material which possesses structural properties which allow for repeated detachable connection to a plurality of modules 50. Further, the material of the handle 30 facilitates the ergonomic advantages of the handle 30 such that the handle 30 is light weight and able to be configured to be readily held in the hand H of a user. The handle 30 preferably is sealed along its exterior openings by seals such as O-rings 39 as shown in FIG. 6 to protect the first cavity 34.

The module 50 preferably is intended to be disposed of after a single use. The module 50, including the module interface 53, is also constructed of a material which possesses structural properties which allow for detachably connecting the module 50 to the handle 30. Further, the module 50 is constructed of a material which is lightweight and allows for manipulation and deflection of the elongate tube 55 within the body 31. Also, the module 50 in its intended single-use capacity is also provided of a material which can be cost effectively disposed of after a single use. As such, the elongate tube 55 is preferably constructed of suitable materials such as a thermoset or a thermoplastic. The module interface 53 also is constructed of suitable materials such as a thermoset or a thermoplastic. Although the handle 30 and fiber optic scope 20 are preferably reusable, a detachable steerable catheter 20 according to the present invention having a disposable handle 30 or fiber optic scope 90 could be provided within the context of the present invention.

Further, the embodiment of FIG. 2 is shown having a plurality of access ports 64, 65, 66 for inserting fluids or medical instruments within a catheter 20 and into a cavity, vessel, or tissue of the human body. By way of example, FIG. 3C illustrates a tube 55 connected within an access port 64 for introducing fluids into the human body B. FIG. 1 illustrates a medical instrument I being inserted through one of a plurality of access ports 64, 65, 66 of the steerable catheter 20 having a disposable module 50 and a sterilizable handle 30 according to the present invention. Further, for example, the elongate tube 55 can also be provided to include at least one lumen 67, 68 which extends from the proximal portion 56 toward the distal end portion 58 of the tube 55 as shown in FIGS. 5 and 12, but stops short of the end of the distal tip 59 of the tube 55. This lumen 67, 68 can be utilized for supplying an air supply for inflating a balloon for various procedures. The elongate tube 55 can be sized having various outer diameters, a plurality of lumens, and lumens having various diameters and shapes.

The diameter of the elongate tube 55 depends on the end application of the detachable steerable catheter 20. In diagnostic visualization and fluid delivery applications, for example, a catheter 20 having an elongate tube 55 having an outer diameter of about 2 mm is preferable. With inserting instruments, suction, irrigation, or procedures utilizing balloons such as angioplasty, for example, an elongate tube 55 having an outer diameter of about 3 to 3.5 mm is preferable. In applications related to urology, for example, an outer diameter of about 2.5 to 3 mm is preferable for the elongate tube 55 of the detachable steerable catheter 20 according to the present invention. The module 50 can also have different durometers and different port functions. As such the detachable steerable catheter 20 according to the present invention is designed to facilitate ease of use in a single hand-held unit.

FIGS. 3A–3D illustrate a series of perspective views of a steerable catheter 20 having a disposable module 50 and a sterilizable handle 30 according to the present invention as well as of a method of detachably connecting this catheter 20. The detachable steerable catheter 20 is preferably detachably connected as follows. First, a sterilized handle 30 and a sterilized fiber optic scope 90 as described above are provided. The handle 30 includes an imaging interface 25 which is preferably connected within the body 31 of the handle 30 such that it extends from within the first cavity 34 of the body 31 through the wall 32 of the body 31 as of illustrated in FIG. 3A and FIG. 6. Preferably, the imaging interface 25 includes a female bayonet connector 26 including opposite grooves 27a, 27b (not shown) for detachably connecting the imaging interface 25 to the proximal end 92 of the fiber optic scope 90. The fiber optic scope 90 includes a male bayonet connector 94 connected to the proximal portion of the fiber optic scope 90. The imaging interface 25 and fiber optic scope 90 connect in a male/female bayonet connection as shown in FIG. 6. The fiber optic scope 90 includes flanges 95a, 95b extending outwardly from opposite sides of the proximal female connector 26 which mate with the grooves 27a, 27b in the image interface 25 to perform the bayonet connection. Various other connectors could also be used as understood by those skilled in the art. The fiber optic scope 90 is detachably connected by sliding the fiber optic scope 90 longitudinally onto the imaging interface 25 as shown in FIGS. 3A and 3D. Other equivalent connections could be provided which would allow for the fiber optic scope 90 to be easily detachably connected. This connection provided, in the preferred embodiment, provides a connection between the imaging bundle and the light source of the imaging interface 25 which interacts with the fiber optics of the fiber optic scope 90.

With the fiber optic scope 90 detachably connected to the handle 30, a disposable module 50 as illustrated in FIG. 3B and described above is also provided. The distal end 93 of the fiber optic scope 90 is preferably coaxially aligned with a lumen 69 in the proximal end of the module 50 as shown in FIG. 3B. The lumen 69 extends from the module interface 53 through the elongate tube 55 to the distal end 59 of the elongate tube 55. The fiber optic scope 90 is slid longitudinally coaxially within the lumen 69 toward the distal portion 58 of the elongate tube 55. The fiber optic scope 90 is sized to extend longitudinally coaxially through the elongate tube 55 from the proximal portion 56 to the distal end portion 58 of the elongate tube 55 within this lumen 69. FIG. 3B shows the module 50 receiving the fiber optic scope 90 within the scope lumen 69 of the module interface 53.

Sliding the module 50 over the fiber optic scope 90 will generally align the module 50 and handle 30 to facilitate detachably connecting them. The module interface 53 and body 31 of the handle 30 are then detachably connected via connection means, e.g., connectors or mating peripheral edges 37, 51. For example, the connecting means could also include ribs and grooves located reciprocally on the module interface 53 and body 31. The module 50 may likewise have ribs on the upper proximal portion and a lower proximal portion. These ribs may detachably connect to grooves connected in the medial portion of the body 31 on an upper surface and on the distal portion on a lower surface of the body 31 with the module connecting means and body connecting means with one comprising ribs and the other comprising grooves whereby the ribs and grooves connect to detachably connect the module 50 to the body 31 of the handle 30. As understood by those skilled in the art, other connecting means could also be used, such as snap fitting connectors. The connecting means could also be located in other portions of the module 50 or handle 30.

The module 50 and handle 30 are connected to provide various structural advantages as described below. Connecting the module interface 53 to the body 31 of the handle 30 preferably will positionally locate or align the controlling means 40 of the handle 30 and the deflecting means 60 of the module 50 for detachably coupling them. The control means 40 and the deflecting means 60 will be detachably connected utilizing a tap engager 75 located on the module 50 as best illustrated in FIGS. 3C and 5. FIGS. 3B, 3C, 5, and 6 show the steps of detachably connecting the module 50 to the handle 30 and coupling the control means 40 of the handle 30 to the deflecting means 60 of the module 50 to actuate manipulation of the elongate tube 55.

An imaging cable 89 preferably is then detachably connected into an image port 36 positioned in the proximal end 30b of the handle 30 as illustrated in FIG. 6. Although conventional male/female connectors preferably are utilized, other connectors also could be utilized. The steerable catheter 20 having a disposable module 50 and sterilizable handle 30 is thus detachably connected for use in the intended medical procedure. Once detachably connected, the detachable steerable catheter 20 according to the present invention provides the medical practitioner with the ability to deflect or manipulate the distal end portions 58 of the tube 55 within a human body B. The detachable steerable catheter 20 also provides the practitioner D with the ability to focus images from within the human body B using focus means 100 connected to the body 31 of the handle 30 of the catheter 20. Further, the medical practitioner D can also insert fluids or medical instruments I into the human body B using this catheter 20.

Upon completion of the medical procedure, the steerable catheter 20 having a disposable module 50 and a sterilizable handle 30 according to the present invention can be easily disconnected. In the preferred embodiment, the tap engager 75 is provided with a detachment knob 78 as shown in FIG. 5. The detachment knob 78 preferably is grasped and activated by pulling, thereby breaking a connection within the module 50 which allows the module 50 to detach from the handle 30. The handle 30 remains equipped to be repeatedly sterilized and receive another sterilized disposable module 50. The module 50 is slidably removed from the fiber optic scope 90 and disposed. The fiber optic scope 90 can then be disconnected in this embodiment by rotating the bayonet connection and sliding the fiber optic scope 90 off the imaging interface 25. The module 50 is preferably discarded, while the fiber optic scope 90 and handle 30 are preferably sterilized for reuse. The imaging cable 89 can be disconnected by unplugging from the port 36.

The detachable connection between the handle 30 and the module 50 provides structural advantages over prior steerable catheters. For example, in the embodiment of the detachable steerable catheter 20 as illustrated in FIG. 1, the elongate tube 55 will not rotate relative to the handle 30 during manipulation of the tube 55 within a human body B. FIG. 7 shows the detachable steerable catheter 20 where the body 31 of the handle 30 has body connecting means, e.g., peripheral edge 37, connected to a medial portion on one surface and a distal portion on an opposite side of the body 31 for detachably connecting to the module interface 53. The module interface 53 includes interface connecting means, e.g., peripheral edge 51, connected to the proximal portion of the module 50 for detachably connecting to the body 31. In FIG. 7, the connecting means is detachably connected to the body connecting means in medial and distal portions of the body 31 such that the body 31 and the module interface 53 define a unitary structure having sufficient stability such that the module 50 remains connected to the handle 30 and the tube 55 does not rotate relative to the handle 30 when the tube 55 is manipulated within the human body B. This stability of the connection is provided by the design of the module 50 and handle 30.

The module connecting means 51 detachably connects to the body connecting means in the medial portion 30c of the body 31 of the handle 30. The proximal portion of the module interface 53 coextensively overlies the body 31 from the distal portion 30a of the body 31 to the medial portion 30c of the body 31 such that the module 50 remains connected to the handle 30 and the tube 55 does not rotate relative to the handle 31 during manipulation of the tube 55 within the human body B as shown in FIGS. 5 through 7. This embodiment has an upper proximal portion of the module 50 overlying the body 31 of the handle 30 to detachably connect at the medial portion of the upper surface of the handle 30 as shown in FIGS. 5 to 7. Other embodiments, however, could be provided with a module 50 extending in a lower or side portion to overlie the body 31 to provide similar structural stability when the tube 55 is manipulated in the human body B. The tube 55 can be rotated 360° about the longitudinal axis defined by the tube 55 by the practitioner rotating the handle 30. As such, the tube 55 can contact the body 31 in various angles and directions further requiring a secure and stable connection. This connection gives the advantage of having the module 50 extend to the medial portion 30C of the body 31 providing stability for the connection. When the tube 55 is manipulated within the body 31, torque can be transferred from the tube 55 to the handle 30.

The shape of the detachable steerable catheter 20 having an elongate tube 55 and handle 30 concentrates stress at the point where the tube 55 and handle 30 connect. For example, the tube 55 could break off or crack if the two components, the module 50 and handle 30, were not securely connected. Further, if the connection were not strong enough, the force and torque caused by manipulation would break the connection such as if the tube 55 was connected to a small portion of the distal end 30a of the handle 30. The connection described also contains many other structural advantages and advantages of ease of use, e.g., ready and ease of assembly.

Further, the module interface 53 preferably has non-uniform proximal edge portions 51 as illustrated which define the proximal end 53a of the module 50 as shown in FIGS. 3B and 3C. The body 31 of the handle 30 preferably has non-uniform edge portions 37 and a wall 32 which preferably transversely extends across the handle body 31. The non-uniform proximal edge portions 37 of the module interface 53 detachably connect to and mate with the non-uniform edge portions of the wall 32 and body 31 of the handle 30 to define a non-uniform continuous boundary between the module 50 and the handle 30 whereby the module 50 is stabilized relative to the handle 30 during manipulation of the tube 55 within a human body as shown in FIGS. 3A–C and FIG. 2.

For added stability, the module 50 as illustrated in FIGS. 2 and 3C also extends in its upper proximal portion in a lateral direction across the body 31 of the handle 30. The lateral portion extends at a width greater than the width of the elongate tube 55 such that the module 50 remains connected to the handle 30 and the tube 55 does not rotate relative to the handle 30 during manipulation of the tube within the human body. The tube can be rotated laterally in a single plane by the deflecting means 60 connected within the elongate tube 55. The entire handle 30 can also be rotated with the tube 55 deflected to rotate in a 360° plane, but for added stability may also only be deflected in a 180° plane. During this movement, stability is needed in the connection between the module 50 and the handle 30.

As described above, in reference to FIG. 2, the detachable steerable catheter 20 according to the present invention further has controlling means 40 for controlling portions of the tube 55 within a cavity, vessel, or tissue of a human body. The control means 40 preferably includes a control wheel 41 which can be rotated to activate control connector means for controlling the deflecting means 40 to manipulate the portions of the tube 55 within a human body B. The body 31 preferably has a recessed portion 23 formed in the outer surface as shown in FIG. 3A. The control wheel 41 preferably is connected in this recessed portion 23 for ease of handling and control. As shown in FIG. 6, the control wheel 41 is substantially positioned within this recessed portion 23 such that the top surface 42 of the control wheel 41 aligns while the horizontal plane of the outer surface of the body 31 forms a unitary horizontal plane. The control wheel 41 is also attached within the recessed portion 23 of the body 31 of the handle 30 at a level whereby the control wheel 41 can be rotated with the fingers of the hand holding the catheter body as shown in FIGS. 1 and 2. The control wheel 41 is connected to the handle 30 on the lower interior surface of the first cavity 34 of the handle 30. This control wheel 41 is positioned so that it may be easily manipulated by the medical practitioner with the hand H which holds the catheter body 31. As illustrated in FIG. 7, the control wheel 41 is rotatably and fixedly connected to the recessed portion 23 of the body 31 for controlling the deflecting means 40 to thereby manipulate distal portions 58 of the elongate tube 55 within a human body B. The control means 40 further has control connector means connected to the control wheel 41 and detachably connected to the deflecting means 40 for connecting the control wheel 41 to the deflecting means 40.

The control wheel 41 is generally circular in shape and has a top surface 42 and a bottom surface 43. The wheel 41 preferably is configured to include an indented portion formed on each opposite vertical side of the control wheel 41 for manipulating the control wheel 41. The indented portions 44 are shaped to receive a practitioner's finger F for rotating the control wheel 41 to manipulate portions of the elongate tube 55 within a human body. Preferably, the control wheel 41 is rotated between a thumb and third finger when the wheel 41 is held in the user's hand as best shown in FIGS. 1 and 2.

The control connector means 40 has deflection linkage wires 81, 82 each respectively connected to a shaft collar 46 of the control wheel 41. The control connector means further has deflection control pins 83 connected to the deflection linkage wires 81, 82 at a distal portion thereof. The deflection control pins 83 extend from the first cavity 34 through the wall 32. The deflection control pins 83 are detachably connected to the deflecting means 40 of the module 50. The control connector means preferably also has deflection springs 84 connected circularly and longitudinally around a medial portion of the deflection control pins 83. The control connector means allows the control wheel 41 to actuate the deflection linkage wires 82, the deflection linkage control pins 83, and the deflection springs 84 to control the deflecting means 40 so as to manipulate a portion of the elongate tube 55 within the body 31.

The control wheel 41 preferably includes a shaft 49 connected to the bottom surface 43 of the wheel 41 at a center axis 45 of the wheel 41 and extending laterally downwardly within the body 31 of the handle 30 as shown in FIG. 7. The shaft 49 is rotatably connected to the body 31 and fixedly connected to the control wheel 41 such that the shaft 49 rotates in unison with the wheel 41 as it rotates. The control wheel 41 illustrated in FIGS. 7–10 further includes the shaft collar 46 extending longitudinally toward the proximal direction of the handle 30. The shaft collar 46 includes a groove or an opening 48 as illustrated.

The deflection linkage wires 81, 82 preferably are fixedly connected to the shaft collar 46 of the control wheel 41 within the groove or opening 48. The deflection linkage wires 81, 82 extend around the control wheel 41 and toward the distal portion of the handle 30 and are fixedly connected to the proximal end of the shaft collar 46. The deflection linkage wires 81, 83 are connected in this embodiment and each includes a hooked portion 86 extending through and around an opening 88 in the proximal portion of the deflection control pins 83. The deflection control pins 83 preferably are connected to the deflection linkage wires 81, 82 and control wheel 41 within the first cavity 34 of the body 31. The deflection control pins 83 are disposed horizontally and extend toward the distal end portion 30a of the body 31. The deflection control pins 83 extend from within the first cavity 34, through the wall 32 of the body 31, and into the second cavity 38 as shown in FIG. 6. Seals such as O-rings 39 preferably are positioned around each deflection control pin 83 between the pin 83 and the wall 32 to seal this opening from fluids and contaminants during use or sterilization.

Disposed around the deflection control pins 83 are the deflection tension springs 84 also illustrated in FIG. 6. The deflection tension springs 84 interact with the wall 32 of the body 31 thereby providing resistance when the control wheel 41 is turned to actuate deflection of the tube 55. The detachable steerable catheter 20 according to an embodiment of the present invention shown in FIG. 8 thereby includes a pair of these deflection control connector systems including the shaft collar 46 of the control wheel 41, deflection linkage wire 82, deflection control spring, 84, and deflection control pin 83 as shown in FIG. 8. This pair of deflection linkage wires 82, deflection tension springs, and deflection control pins 83 are disposed on each side of the longitudinal axis of the body 31 shown in FIG. 8. The deflection control pins 83 each contain an opening 89 in the distal portion of the control pin 83 to receive the deflection means 40. The opening 89 laterally receives a steering wire end 73 located in the module 50.

The handle 30 preferably is sealed in all openings. The openings where the control wheel 41 and focus wheel 100 protrude from the body 31 also are sealed. In the embodiment of the present invention shown in FIGS. 7–10, O-rings 48a are located between the control wheel 41 and the body edge portions and between the focus wheel 100 and the body edge portions for sealing the handle body 31 during use and sterilization. O-rings 39 are also positioned around the opening in the wall 32 of the body 31 where the deflection control pins 83 extend through the wall 32 of the body 31 portion shown in FIG. 7.

The detachable steerable catheter 20 according to the present invention further includes deflecting means 60 connected within the module 50. These deflecting means 60 are shown in FIGS. 8–12. The embodiment illustrated in these figures shows the deflecting means 60 comprises pairs of steering wires 61, 62 having distal portions connected to the distal portions of the elongate tube 55 and proximal portions connected to the module interface 53. As the steering wires 61, 62 preferably are identical, they will be described in reference to one steering wire 61 or 62 where appropriate. The proximal portions of the steering wires 61, 62 preferably are positioned along a proximal portion of the module interface 53. The module interface 53 is detachably connected to the body 31 such that proximal ends 73 of the steering wires 61 62 are detachably connected to the control means 40 to thereby manipulate distal end portions 58 of the distal elongate tube 55 positioned within a human body B when the control means 40 are operatively activated.

As shown in FIG. 4, the steering wires 61, 62 extend from the lumen 67 of the module 50 and each includes a steering wire end 73. The steering wires 61, 62 preferably are positioned generally parallel to one another in the module 50. The steering wire ends 73 preferably are positioned on opposite sides of the scope lumen 69 of the tube 55. The steering wire ends 73 include a leg 71 which extends laterally from the module interface 53 and a post 54 disposed at the lateral edge portion of the steering wire end 73. The post 54 extends downwardly so that when the module 50 and handle 30 are detachably connected, the post 54 is aligned to be received within the opening 89 of the deflection control pin 83.

FIGS. 11 and 12 illustrate the portions elongate tube 55 of the steerable catheter having a disposable module and a sterilizable handle and the construction of the steering wires 61, 62. The steering wires 61, 62 extend through wire lumens in the elongate tube 55 to the distal end portion 58 of the elongate tube 55. In the distal end portion 58 of the tube 55, the steering wires 61, 62 are looped and extend parallel to each other in an upper and lower portion of the tube 55 as shown in FIG. 12. FIG. 12 is an enlarged cross-sectional view illustrating the insertion of the steering wires 61, 62 prior to the forming of the tip (illustrated in phantom view) of the distal end portion 58 of the tube 55. Pairs of upper steering wire lumens and lower lumens are positioned on opposite sides of the working lumens 67, 68 and scope lumen 69 within the tube 55 as shown in FIG. 11. The steering wires 61, 62 are inserted into the wire lumens of the various portions of the tube 55 and form loops in the distal end portion 58. The steering wires 61, 62 preferably are fixed to the elongate tube 55 so that the movement of the control wheel 41 responsively moves the steering wires 61, 62 to thereby bend and manipulate the tube 55. Numerous techniques can be used to fix the steering wires 61, 62 to the elongate tube 55 such as RF welding or welding ends of the wires 61, 62 to a portion such as the distal portion 58 of the elongate tube 55.

These techniques are understood by those skilled in the art. As illustrated in the embodiment of FIG. 12, the looping of the steering wires 61, 62 through the wire lumens of the distal end portion 58 of the tube 55 secures the steering wires 61, 62 to a portion of the elongate tube 55 and also reduces the slippage of the steering wires 61, 62 as the steering wires 61, 62 are moved longitudinally with respect to one another to manipulate the various portions of the elongate tube 55. FIG. 11 illustrates the location of the working lumens 67, 68, the scope lumen 69, and the steering wire lumens extending parallel to the axis of the coaxial proximal medial and distal portions and the steering wires 61, 62 positioned within the elongate tube 55.

As the control wheel 41 is actuated in one direction and thereby moves the control connector means in the same direction, the steering wires 61, 62 are moved to deflect the elongate tube 55 under tension in that direction. The tube 55 can be deflected in an arced path along about a 180° path. Various deflecting means other than steering wires 61, 62 positioned in the elongate tube 55 are known and could be incorporated within this embodiment of the detachable steerable catheter 20 as understood by the present invention.

The embodiment shown in FIGS. 5–20 further illustrates a module 50 including an engaging means 75 for detachably engaging the deflecting means 60 of the module 50 and the control means 40 of the handle 30 after the module 50 is detachably connected to the handle 30. This engaging means preferably is pivotally connected to the module interface 53. The engaging means is movable between a first disengaged position and a second engaged position. In the first disengaged position, the engaging means is not in contact with the deflecting means 60, and the deflecting means 60 and the control means 40 are not detachably connected as illustrated in FIG. 5. Therefore, in the first disengaged position, the distal end portion 58 of the elongate tube 55 cannot be manipulated by actuating the control means 40.

In the second engaged position, the engaging means 75 guides or moves the deflecting means 60 to detachably connect to the control means 40. The engaging means 75 is pivotally moved to the second engaged position whereby the engaging means 75 engages the deflecting means 60 and detachably connects the deflecting means 60 to the control means 40 such that the control wheel 41 can be actuated to control the deflecting means 40 for manipulating the distal portion of the tube 55 in the human body B.

As shown in FIG. 5, the engaging means 75 preferably has a tap 79 including a grip portion 75, 78 and an arm portion 74 hingedly connected to the module interface 53. In the unengaged position, the arm portion 74 is not in contact with the steering wire ends. The arm portion 74, however, is positioned such that when the grip portion 78 is grasped and the tap 79 is pivoted, the arm 74 moves in a generally downward direction toward the center of the opening 89. The arm portion 74 engages the steering wire end 73 and forces the post 54 of the steering wire end 87 into the opening 89 of the control pin 83 as shown in FIGS. 7 and 8. When the tap 79 is fully extended, a detachable locking connection is formed between an edge portion of the tap 79 and an edge of the outer surface of the module 50 forming a single planar surface which preferably seals the module 50 from exposure to fluids, viruses, bacteria, and other elements.

The module 50 is provided with a tap 79 constructed of a suitable material for rotating from the disengaged to the engaged position described herein. Preferably, this portion of the module 50 is constructed from a flexible plastic which pivots without cracking or breaking. The tap 79 is integrally formed with the module 50. In the engaged position as shown in FIG. 8, the steering wire posts 54 are detachably connected within the openings 89 of the control pin 83. As further shown in FIG. 7, the steering wire ends 73 remain detachably connected within the openings 89 of the control pin 83 by the locking connection of the tap 79 with the edge of the outer surface of the body 31.

As such, the control wheel 41 can be rotated to deflect and manipulate portions of the elongate tube 55 within the human body B. As described, deflection of the distal end portion 58 of the elongate tube 55 occurs in a horizontal plane of 180° rotation. Manipulation can be actuated rotatably in vertical arc of 360° about the longitudinal axis of the tube 55 by rotating the hand H holding the handle 30 in either a clockwise or counterclockwise direction.

As shown in FIGS. 2 and 3A–C, the detachable steerable catheter 20 according to the present invention has a module interface including an upper proximal portion which connects to the medial portion 30C of the handle body 31. The module 50 includes a plurality of access ports 64, 65, 66. The ports are connected within the upper proximal portion and positionally aligned with at least one of the lumens 67 in the elongate tube 55 for accessing at least one lumen 67 therefrom. The tube 55 has at least one lumen 67 which extends from the proximal end portion 56 of the elongate tube 55 to the distal end portion 50 of the tube. The elongate tube 55 has an opening 96 in the distal end portion shown in FIG. 12. At least one lumen 67 is coaxially aligned with an opening in the distal tip 96 of the elongate tube 55 defining at least one, and preferably two or more, open channel extending from the access ports 64, 65, 66 through the lumen 67 into the opening for inserting fluids and instruments into the human body B.

The embodiment of the steerable catheter having a disposable module and a sterilizable handle according to the present invention as illustrated in FIGS. 2 and 3A–3D includes three access ports 64, 65, 66 positioned in the upper surface of the module interface 53. These access ports 64, 65, 66 are positionally aligned with two lumens 67, 68 defining relatively straight channels whereby medical instruments I and fluids can be inserted through the access ports 64, 65, 66 into the lumen 67, 68 extending substantially straight from a user toward a distal end portion 58 of the tube 55.

FIG. 3B, for example, shows this straight channel formed from the access port into the lumen. The embodiment shown in FIG. 3B in combination with FIGS. 4 and 11 show three access ports 64, 65, 66 going through a manifold 120, best illustrated in FIG. 4, into two upper lumens 67, 68 as shown in FIG. 11. The catheter 20 according to the present invention can be provided with various numbers of access ports 64, 65, 66 and lumens 67, 68, 69. Further, the catheter 20 can be provided without a manifold 120 having equal numbers of ports and lumens. The catheter 20 according to the present invention, however, preferably has at least one working lumen 67 or 68 and one scope lumen 64 for the fiber optic scope 90.

As shown in FIG. 3B, various attachments such as a fluid tube 132 with a standard medical luer lock 134 attached to its distal end can be connected within an access port 64 such that a medical device or apparatus such as an IV fluid tube can be connected to the luer lock 134 and inserted into the access port 64 and the elongate tube 55.

As shown in FIG. 4, the module 50 includes a module interface 53 having a manifold 120 whereby piping connectors 122, 123, 124 extend from the access ports 64, 65, 66 into the lumens 67, 68 of the tube 55. FIG. 4 shows three upper lumens 122, 123, 124 for inserting fluid and/or instruments. FIG. 4 further shows a scope lumen 69 located below the working lumens 67, 68 for inserting a fiber optic scope 90 within the elongate tube 55. A preferred embodiment contemplates a module 50 having a manifold 120 positioned within the module 50. The manifold 120 includes a piping connector 121 having a plurality of openings connecting a plurality of the access ports 64, 65, 66 to at least one or a lesser number of the lumens 67, 68 of the elongate tube 55. The access ports 64, 65, 66 and the lumens 67, 68 are positionally aligned on opposite ends of the openings of the piping connector 121 defining a relatively straight channel whereby medical instruments I and fluids can be inserted through the access ports 64, 65, 66 into the lumen 67, 68 extending substantially straight from a user toward a distal end of the tube 55.

The module 50 is further provided with an upper face which includes a recessed portion 59. The access ports 64, 65, 66 preferably are positioned in an opening in the module interface 53 within this recessed portion as illustrated. In a preferred embodiment, as shown in FIG. 3B, the outward openings of the access ports 64, 65, 66 align with the upper surface of the recessed portion 59 defining a generally unitary plane between the access port openings and the surface of the recessed portion 59 of the upper face. The position of these access ports 64, 65, 66 in this recessed portion 59 is advantageous for inserting both medical instruments I and fluids as well as attaching a medical device or apparatus and connectors such as the tube 132 with luer lock 134 shown in FIG. 3B.

The catheter 20 according to the present invention is provided in a preferred embodiment with an angled handle 30. The catheter 20 includes a handle 30 detachably connected to the module 50 and configured to be readily held in the hand H of a user. The handle 30 has a body 31 including proximal 30b, medial 30c, and distal 30a portions. The body 31 preferably angles, as shown in FIG. 6, from the proximal portion toward the distal portion along an upper surface and a lower surface of the body 31. This angling of the handle defines an angle θ, e.g., preferably between 5°–60°, between the tube 55 and the portion of the body 31 held by the medical practitioner for facilitating inserting the catheter 20 into a vessel, cavity, or tissue of the human body.

Various surgical and diagnostic procedures require inserting the detachable steerable catheter 20 into openings at various angles. The angled handle 30 facilitates the medical practitioner's ability to maintain his hand, wrist, and forearm in an advantageous straight alignment allowing the angle of the handle 11 to position the tube 55 within the opening. This facilitates both the ease and precision of use, as well as comfort for the patient and practitioner. Also, this angling provides other ergonomic advantages such as reducing fatigue on the practitioner during lengthy or repeated procedures. Various angled configurations could be provided having the ergonomic advantages of the preferred embodiment.

Other ergonomic advantages are provided by the catheter 20 according to the present invention. For example, the distribution and weight of the catheter 20 according to the present invention is such that it can effectively be used as a single hand-held unit. The angling and weight distribution of the catheter also enhance the usability of the control wheel 41 and focus wheel 100. The catheter 20 according to the present invention is designed such that the focus wheel 100 and control wheel 41 can be simultaneously activated to manipulate the elongate tube 55 as illustrated in FIG. 2.

Further, the detachable steerable catheter 20 according to the present invention, as illustrated in FIG. 8, comprises a body 31 including vertical sides. The body 31 tapers inwardly from the distal portion 30a toward a medial portion 30c along the vertical sides and from a proximal portion 30b toward a medial portion 30c along the vertical sides. This taper also facilitates holding and manipulation of the detachable steerable catheter 20 by a single hand. The embodiment illustrated includes a narrow portion enabling the practitioner to grip the handle 30 around the medial portion 30c between the thumb and fingers to rotatively control the control wheel 41.

The handle 30 is also provided to be held near the medial portion 30c of the body 31 with the weight distribution such that the handle 30 remains balanced within the practitioner's palm during use. Such a long instrument as the catheter 20, if not balanced, would tend to flop in a forward or rearward direction out of the practitioner's hand during use. Further the catheter 20 is lightweight. The handle 30 material preferably includes a thermoplastic or a thermoset or a metal/metal alloy (such as aluminum or stainless steel). Various other angled handle 11 configurations could be provided with the described ergonomic advantages.

The steerable catheter having a disposable module and a sterilizable handle according to the present invention also has imaging means 150 positioned within the body 31 of the handle 31 for transmitting images from within the human body B to an external viewing apparatus such as a monitor or CRT as shown in FIGS. 3A–3D and 7–10. The medical practitioner can thereby view a space within the human body B while simultaneously conducting medical procedures or diagnosis.

FIG. 7 illustrates a steerable catheter 20 having a disposable module and a sterilizable handle according to the present invention with an imaging cable 89 detachably connected to the imaging means 150, such as an internally disposed camera 156 and internal interface cable 157, through an opening or port 36 in the proximal end portion 30*b* of the handle 30. The imaging cable 89 extends outwardly from the catheter 20 and connects at its opposite end to a viewing monitor or CRT as known in the art for transmitting images from within the human body for viewing on the attached monitor.

An embodiment of the detachable steerable catheter 20 according to the present invention preferably includes imaging means which includes a camera 156 positioned within the first cavity 34 of the body 31 of the catheter 20 for capturing and transmitting images from within the body as illustrated in FIGS. 7–10. The handle 31 is sealed to protect the camera 156 from contaminants. The camera 156 also is sealed to withstand sterilization and use without damaging the camera. Although not preferable, other imaging means such as an external camera could be used in conjunction with the detachable steerable catheter 20 to capture and transmit images from within the human body during the medical procedure according to the present invention.

The imaging interface cable 157 includes an image bundle and light source bundle. The imaging interface cable 157 connects to the proximal portion of the camera 156 and extends rearwardly around the shaft 49 of the focus wheel 100 and control wheels 41 as illustrated in the fragmentary sectional view of FIG. 9. The imaging interface cable 157 extends further rearwardly and connects to the image connector 159 positioned in the image port located in the proximal opening of the handle 31 as shown in FIG. 7. This image connector connects to the external imaging cable 89 which includes a corresponding light source and image bundle for transmitting images from within the human body B to the external monitor.

The imaging interface 25 preferably is connected to the distal end of the camera 156. The imaging interface 25 preferably extends through the wall 32 of the body 31. As illustrated in FIG. 8, the camera 156 is disposed within the proximal portion of the handle body 31 and within the first cavity 34. The camera 156 is also disposed between the control connector means as also shown in FIG. 8. The camera 156 extends rearwardly toward the medial portion of the body 31. The imaging interface cable 157 extends rearwardly around the shaft 49 of the control wheel 41 to connect with the image cable 89 in the proximal opening 36 of the detachable steerable catheter 20 as illustrated in FIG. 9.

A preferred embodiment of the steerable catheter 20 having a disposable module and a sterilizable handle according to the present invention is utilized with a fiber optic scope 90 as described in connection with FIGS. 3A through 3D. Other means of projecting light or receiving images, however, could also be provided. Fiber scopes of varying dimensions can be provided to match various sized elongate tubes utilized for different procedures. The fiber optic scope 90 provided is preferably between 8 and 14 inches in length. In a preferred embodiment, such as illustrated in FIG. 6, the fiber optic scope 90 connection with the imaging interface 25 aligns the fiber optic material, e.g., along flange 94*a*, of the fiber optic scope 90 with the light source bundle and camera 156 connected to the handle imaging interface. The fiber optic scope 90 comprises a portion of fiber optic material which is centered on the camera 156. The fiber optic scope 90, or fiber scope, is also aligned with light sources within the imaging interface. The fiber scope 90 magnifies the light transmitted down the length of the elongate tube 55 from the light source. Further, the fiber optic scope 90 receives images from within the human body B and transmits them to the camera 156 connected to the fiber optic scope 90.

In conjunction with the imaging means of a preferred embodiment, the detachable steerable catheter 20 also has focus means 100 for focusing images transmitted from within the human body during a medical procedure or diagnosis. This focus means 100 preferably includes a focus wheel 101 having a top surface and a bottom surface whereby images are easily adjusted or focused using a single finger F to rotate the top surface of the wheel 101 as shown in FIG. 2. The focus wheel 101 includes an indentation 104 configured to receive a finger F as shown in FIGS. 2 and 3 for rotating the focus wheel 101 to focus images transmitted from within the human body. The medical practitioner can thereby easily focus the images transmitted from within the human body on the catheter 20 while viewing the images on the attached monitor.

The focus wheel 101 preferably is positioned on the upper surface of the body 31 in proximity to the deflecting control wheel 41 such as to facilitate focusing and controlling by a single hand H of the practitioner or by another practitioner. The catheter 20 according to the present invention overcomes prior problems of focusing an external camera requiring moving away from the space of the actual procedure or relying on another practitioner or assistant for focusing.

The focus means 100 further includes a focus connector fixedly connected to a bottom surface of the focus wheel 101 such that the shaft 108 and the focus wheel 101 rotate in unison (see FIG. 9). The shaft 108 extends downwardly within the first cavity 34 of the body 31 and is connected to the body 31 on the bottom of the body 31.

The control wheel 41 contains a recessed center portion of the upper surface. The focus wheel 101 is positioned concentrically within this recessed portion of the control wheel 41 as illustrated in FIG. 10. The focus wheel 101 is connected to the body 31 in the recessed portion of the control wheel 41 such that the focus wheel 101 and the control wheel 41 define generally concentric circles and are aligned defining a generally common center portion of each wheel with the imaging focus wheel 101 having a smaller diameter than the control wheel 41. The focus wheel 101 and control wheel 41 rotate independently. Various other shapes and configurations of this catheter 20 having a focus wheel 101 according to the present invention could be provided. The upper surface of the focus wheel 101 and the control wheel 41 preferably form a unitary plane.

FIGS. 7, 8, 9, and 10 illustrate other aspects of an embodiment of the focusing means. The focusing means further comprises, in this embodiment, a focus cable 109 connected to the shaft 108 of the focus wheel 101. The camera 156 includes an imaging focus means which when actuated by rotating the focus wheel 101 rotates to focus the images. This allows the focus wheel 101 to be rotated beyond a full 360° in a single direction to facilitate focusing. Preferably, when the focus wheel 101 is turned beyond about 15°–30°, e.g., about 22.5°, for example, the image is inverted and the imaging means continues to focus the image as viewed. FIG. 9 shows the focus cable 109 connected to the shaft 108 of the focus wheel 101 for translating the rotational movement of the focus wheel 101 into linear movement of focusing a focus cell or other means within the cavity 34 for focusing the image.

The steerable catheter having a disposable module and a sterilizable handle according to the present invention can also be supplied in another embodiment as a catheter kit 200. The detachable steerable catheter kit 200 provides a catheter 20 for inserting at least portions into a vessel, cavity, or tissue of the human body B to thereby provide disposability and manipulation of a portion of the catheter 20 when positioned within the vessel, cavity, or tissue. The kit 200 comprises a plurality of disposable modules 50 and a reusable handle 30 for detachably connecting to the modules 50. The handle 30 is configured to be readily held in the hand H of a user as described above.

The detachable steerable catheter kit 200 further comprises a fiber optic scope 90 which can be detachably connected to the handle 30 and positionable within the module 50 as previously described. The module 50 of this kit 200 would include an elongate tube 55 having at least one lumen 67, 68 extending from a distal end 58 to the proximal end 56 of the tube 55, a module interface 53 connected to the proximal end 56 of the tube 55, and deflecting means 60 connected to the tube 55 for deflecting the distal portion of the elongate tube 55. The reusable handle 30 has a body 31 including a wall 32 positioned in distal portions of the body 31; the wall 32 has an outer surface thereof defining an exterior portion of the body 31. A first cavity 34 is formed within the body 31. The body 31 is detachably and extensively connectable to the module interface 53 through the outer surface of the wall 32. The handle 30 also has control means 40 connected to the body 31 and detachably connected to the deflecting means 60 of the module 50 for responsively controlling the deflecting means 60 to thereby manipulate distal portions of the elongate tube 55. The control means 40 and deflecting means 60 define a unitary catheter manipulation means extending from the first cavity 34 through the wall 32 and to the tube 55 for manipulating a distal portion of the catheter 20 when positioned in a vessel, cavity, or tissue.

This catheter kit 20 is illustrated in FIGS. 13 and 14. FIG. 13 illustrates a module 50 as described above sealed within a plastic packaging. FIG. 14 illustrates a plurality of these disposable individually sealed modules 50 inserted within a package with a sealed reusable handle 30 and a sealed reusable fiber scope 90 both as explained previously. Other configurations of the kit 200 can be sold. For example, a kit can be sold without a fiber scope 90 or with a plurality of varying sized fiber scopes 90 and modules 50. As indicated, the fiber optic scope 90 and module 50 vary in length, diameter, and configuration according to the end application. This kit 200 will facilitate ease of use as a catheter 20 and included camera 156 which can all be shipped, stored, and used in a small space. The catheter kit 20 according to the present invention also provides the advantage of saving space such as during shipping, storage, and use.

The present invention also includes methods of connecting and using a catheter 20 as described above and as illustrated in the drawings. A method of detachably connecting a catheter 20 having a handle 30 which includes a body 31 and a detachable module 50 which includes an elongate tube 55 having at least one lumen 67, 68, 69 extending therethrough is provided by the present invention. This method preferably includes connecting a fiberscope 90 to a distal end portion of the body 31 of the handle 30, positioning the fiberscope 90 into the at least one lumen 69 of the tube 55 of the module 50, and connecting the module 50 to the body 31 of the handle for viewing portions of a vessel, cavity, or tissue when a distal end of the tube 55 is positioned therein.

The catheter 20 and methods of the present invention further provide a detachable catheter with a reusable fiber optic scope 90 which can be detachably connected to the handle 30 and sealed within the detachable module 50 during a medical procedure. A steerable catheter 20 having a disposable module 50 and a sterilizable handle 30 according to the present invention also can advantageously be provided in a kit 200 which, for example, includes a plurality of detachable, disposable modules 50 and a reusable handle 30 and also may include a fiber optic scope 90 to be used with the disposable modules. The kit 200, for example, provides the practitioner with an apparatus and method which allow a first module 50 to be connected to the handle 30 for use in a cavity, vessel, or tissue during a medical procedure such as a gynecological, epidural, neurological, nose, brain, cardiovascular, thoracic, or other procedure as understood by those skilled in the art. The first module 50 can then be disconnected and disposed of by placing it into a sanitary container or other means of properly disposing of a used and/or contaminated device. The handle 30 can then be sterilized and a second module, e.g., sterile module from the kit 200, connected to the body 31 of the handle 30.

The handle 30 of a steerable catheter 20 according to the present invention can further include the angled handle that provides entry, e.g., preferably along a substantially straight axis, into a portion of the human body while allowing the medical practitioner to grasp the steerable catheter in an advantageous hand position. A detachable steerable catheter 20 can also advantageously include the camera 156 mounted internally in the handle of the catheter wherein the handle can be sterilized with the camera therein and the camera is protected from breakage or contamination therein. A steerable catheter and methods according to the present invention further can provide a steerable catheter having a focus means positioned on the handle of the catheter for focusing the internal camera positioned within the handle. A steerable catheter 20 and methods of the present invention also advantageously provide a disposable module and a sterilizable handle having a focus wheel and control wheel disposed such that the focus wheel and control wheel can be simultaneously adjusted by the same hand of the practitioner.

In the drawings and specification, there have been disclosed preferred embodiments of the invention, and, although specific terms are employed, these terms are used in a descriptive sense only and not for purposes of limitation. The invention has been described in considerable detail with specific reference to various illustrated embodiments. It will be apparent, however, that various modifications and changes can be made within the spirit and scope of the invention as described in the foregoing specification and defined in the appended claims.

That which is claimed:

1. A method of detachably connecting a catheter having a handle and a detachable module, the module including an elongate tube having at least one lumen extending therethrough and the handle including a body, the method comprising:

connecting a fiberscope to a distal end portion of the body of the handle;

positioning the fiberscope into the at least one lumen of the tube of the module; and connecting the module to the body of the handle for viewing portions of a vessel, cavity, or tissue when a distal end of the tube is positioned therein.

2. A method as defined in claim 1, further comprising capturing images of portions of a vessel, cavity, or tissue from an image capturing device positioned within the body of the handle.

3. A method as defined in claim 2, further comprising focusing the images captured by said image capturing device from a focusing device connected to the body of the handle.

4. A method of using a catheter positioned in a hand of a user, the catheter having portions thereof positioned within a cavity, vessel, or tissue of a human body, the catheter including a handle configured to be readily held in a hand of a user and having a body, an elongate tube connected to and extending outwardly from the body of the handle, the elongate tube having at least one lumen extending therethrough from a proximal end portion to a distal end portion thereof, and a manipulator connected to the body of the handle and a distal end portion of the elongate tube, the method comprising:

positioning the elongate tube into a cavity, vessel, or tissue of a human body;

manipulating a distal end portion of the elongate tube responsive to a hand of a user holding the handle;

capturing an image of portions of a cavity, vessel, or tissue from the tube positioned in a cavity, vessel, or tissue; and focusing the images captured responsive to the same hand of the user during operative holding of the handle.

5. A method of using a catheter positioned in a hand of a user, the catheter having portions thereof positioned within a cavity, vessel, or tissue of a human body, the catheter including a handle configured to be readily held in a hand of a user and having a body, a module having an elongate tube including at least one lumen extending therethrough from a proximal end portion to a distal end portion thereof, and a manipulator connected to the body of the handle and a distal end portion of the elongate tube, the method comprising:

connecting a fiberscope to a distal end portion of the body of the handle;

positioning the fiberscope into the at least one lumen of the tube of the module;

connecting the module to the body of the handle;

positioning the elongate tube into a cavity, vessel, or tissue of a human body;

manipulating a portion of the elongate tube responsive to a hand of a user holding the handle;

capturing an image of portions of a cavity, vessel, or tissue through the fiberscope; and focusing the images captured responsive to the same hand of the user during operative holding of the handle.

6. A method of detachably connecting a catheter having a handle and a detachable module, the module including an elongate tube having at least one lumen extending therethrough and the handle including an angled body, the method comprising:

connecting the module to the angled body of the handle;

positioning the elongate tube into a cavity, vessel, or tissue of a human body;

capturing an image of portions of a cavity, vessel, or tissue from the tube positioned in a cavity, vessel, or tissue; and focusing the images captured responsive to the same hand of the user during operative holding of the handle.

7. A method as defined by claim 6, further comprising the step of coaxially inserting an instrument into a lumen of the elongate tube along a substantially straight axis with the other hand of the user.

8. A method of detachably connecting a catheter having a handle and a plurality of detachable and disposable modules, each module including an elongate tube having at least one lumen extending therethrough and the handle including a body, the method comprising:

connecting a first module to the body of the handle for use in a vessel, cavity, or tissue during a medical procedure;

disconnecting the first module from the handle; and connecting a second module to the body of the handle for use in a vessel, cavity, or tissue during a medical procedure.

* * * * *

UNITED STATES PATENT AND TRADEMARK OFFICE
CERTIFICATE OF CORRECTION

PATENT NO. : 5,846,221
DATED : December 8, 1998
INVENTOR(S) : Snoke et al

It is certified that error appears in the above-identified patent and that said Letters Patent is hereby corrected as shown below:

On the title page: Item

[62], Related U.S. Application Data

Strike:
"Pat. No. 5,820,590."

Insert:
--Pat. No. 5,860,953.--

Signed and Sealed this

Thirtieth Day of March, 1999

Attest:

Q. TODD DICKINSON

Attesting Officer

Acting Commissioner of Patents and Trademarks